United States Patent
Hiraide et al.

(10) Patent No.: US 7,645,864 B2
(45) Date of Patent: Jan. 12, 2010

(54) ERYTHROMYCIN DERIVATIVE HAVING NOVEL CRYSTAL STRUCTURES AND PROCESSES FOR THEIR PRODUCTION

(75) Inventors: Akira Hiraide, Tokyo (JP); Kaichiro Koyama, Tokyo (JP); Hitoshi Shimizu, Tokyo (JP); Kaname Tsuzaki, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/399,146

(22) PCT Filed: Oct. 12, 2001

(86) PCT No.: PCT/JP01/08990

§ 371 (c)(1),
(2), (4) Date: Apr. 14, 2003

(87) PCT Pub. No.: WO02/30943

PCT Pub. Date: Apr. 18, 2002

(65) Prior Publication Data

US 2003/0191296 A1    Oct. 9, 2003

(51) Int. Cl.
*C07H 17/08*    (2006.01)

(52) U.S. Cl. ............................................. 536/7.2
(58) Field of Classification Search ............. 536/7.2, 536/18.5
See application file for complete search history.

(56) References Cited

U.S. PATENT DOCUMENTS 5,959,088 A     9/1999  Miura et al.
6,225,287 B1 *  5/2001  Edvardsson et al. ........... 514/19

FOREIGN PATENT DOCUMENTS

EP    0 643 068 A1    3/1995
EP    0 846 697 A1 *  6/1998

* cited by examiner

*Primary Examiner*—Elli Peselev
(74) *Attorney, Agent, or Firm*—Browdy & Neimark, PPLC

(57) ABSTRACT

The present invention provides an E-type crystal of N-demethyl-N-isopropyl-12-methoxy-11-oxo-8,9-anhydroerythromycin A-6,9-hemiacetal fumarate having strong diffraction peaks at diffraction angles (2θ) of 5.6° and 10.4° as measured by powder X-ray diffractometry, which is prepared by treating a C-type crystal of the compound in a mixed solvent of ethyl acetate and water at 20° C. to 40° C., and a D-type crystal prepared via the E-type crystal. These crystals have a reduced content of residual solvent and high suitability for formulation.

5 Claims, 5 Drawing Sheets

ERYTHROMYCIN DERIVATIVE HAVING NOVEL CRYSTAL STRUCTURES AND PROCESSES FOR THEIR PRODUCTION

PRIORITY

The present application is a 371 of PCT/JP01/08990, filed Oct. 12, 2001.

TECHNICAL FIELD

The present invention relates to novel crystals of fumarate salts of erythromycin derivatives and a method for their preparation.

BACKGROUND ART

The compound represented by formula (I):

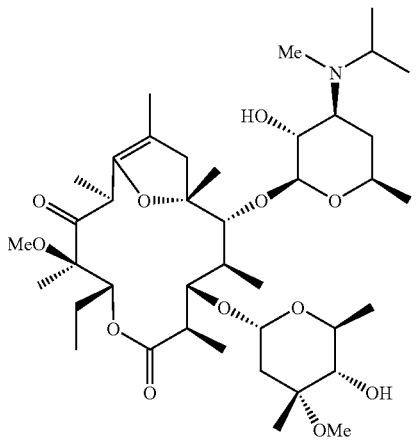

is disclosed in, for example, JP 6-56873 A (WO93/24509) and JP 9-100291 A (WO97/06177). This compound is known to have the ability to enhance the movement of the digestive tract.

The preparation of this compound is disclosed in, for example, JP 9-100291 A, Bioorg. & Med. Chem. Lett. vol. 4(11), 1347 (1994) and JP 9-100291 A.

Conventionally, there are three patterns for crystals of a fumarate salt of compound (I): A-type crystal (hereinafter simply referred to as "A-type crystal"), C-type crystal (hereinafter simply referred to as "C-type crystal") and D-type crystal (hereinafter simply referred to as "D-type crystal"). Each of the A-type, C-type and D-type crystals is disclosed in JP 9-100291 A and can be prepared as described in this publication.

The A-type crystal may be prepared from a fumarate salt of compound (I) through recrystallization from a mixed solvent of methanol and isopropanol. The molar ratio between compound (I) and fumarate is 2:1. The A-type crystal provides the diffraction pattern as shown in FIG. 1 when measured by X-ray diffractometry with Cu—Kα radiation.

The C-type crystal may be prepared from a fumarate salt of compound (I) through treatment with ethyl acetate. The molar ratio between compound (I) and fumarate is 1:1. The C-type crystal provides the diffraction pattern as shown in FIG. 2 when measured by X-ray diffractometry with Cu—Kα radiation.

The D-type crystal may be prepared from a fumarate salt of compound (I) through treatment with a mixed solvent of ethyl acetate and water. The molar ratio between compound (I) and fumarate is 2:1. The D-type crystal provides the diffraction pattern as shown in FIG. 3 when measured by X-ray diffractometry with Cu—Kα radiation.

Among the A-type, C-type and D-type crystals, the D-type crystal is reported to have high quality as a pharmaceutical and a starting material therefor because it is superior in stability or other properties to the other crystals (JP 9-100291 A).

However, the prior art D-form crystal prepared by the conventionally known techniques as mentioned above which involve the following problems: a large volume of crystallization solvent remains in the crystal as a residual solvent; the residual solvent is difficult to remove during drying procedure; and the dryness of residual solvent cannot be below 1500 ppm. In this case, the residual solvent remaining in the D-form crystal is ethyl acetate, which is less toxic and less risky for human health (see "Guideline for residual solvents in pharmaceuticals" attached to the Notification No. 307 of Mar. 30, 1998 delivered from the director of Evaluation and Licensing Division, Pharmaceutical and Medical Safety Bureau, Ministry of Health and Welfare, Japan). However, it is naturally more desirable to reduce the content of such a less toxic solvent remaining in the crystal in a case where the crystal is intended to be used as a starting material for pharmaceuticals. Preferably, the content of residual solvent should be reduced to 1500 ppm or below, more preferably 1000 ppm or below. The prior art D-form crystal also involves another problem of having a small particle size, which often leads to tabletting troubles during the preparation of tablets comprising this crystal.

DISCLOSURE OF THE INVENTION

As a result of extensive and intensive efforts made to overcome the above problems in the prior art, the present inventors found structurally novel crystals of a fumarate salt of compound (I), which were different from known crystals, and finally completed the invention based on this finding.

Namely, the present invention is directed to an E-form crystal of a fumarate salt of the compound represented by formula (I):

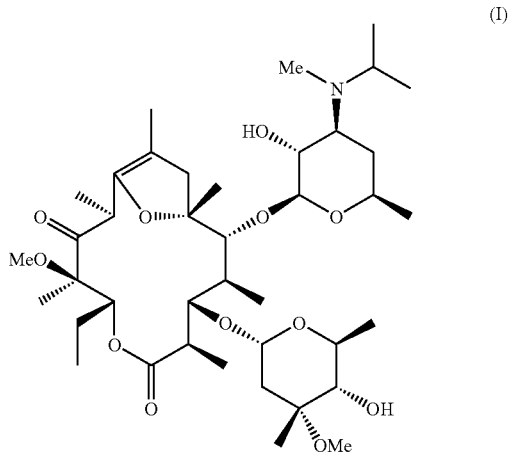

wherein said E-form crystal has strong X-ray diffraction peaks at diffraction angles (2θ) of 5.6° and 10.4° as measured by X-ray diffractometry with Cu—Kα radiation.

The present invention is also directed to a method for preparing an E-form crystal of a fumarate salt of the compound represented by formula (I):

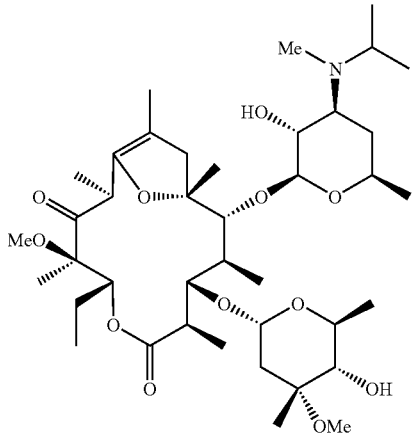

(I)

which comprises treating a C-type crystal of a fumarate salt of compound (I) in a mixed solvent of ethyl acetate and water at 20° C. to 40° C., wherein said E-form crystal has strong X-ray diffraction peaks at diffraction angles (2θ) of 5.6° and 10.4° as measured by X-ray diffractometry with Cu—Kα radiation.

Further, the present invention is directed to a D-form crystal of a fumarate salt of the compound represented by formula (I):

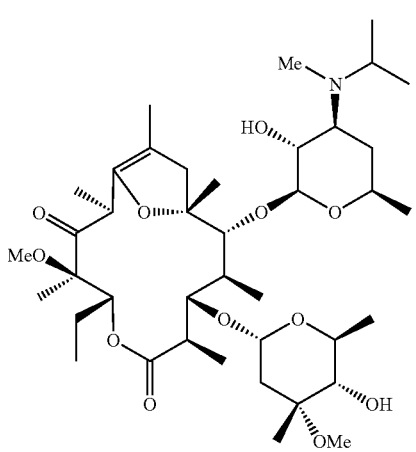

(I)

which is obtainable via an E-form crystal of a fumarate salt of compound (I) having strong X-ray diffraction peaks at diffraction angles (2θ) of 5.6° and 10.4° as measured by X-ray diffractometry with Cu—Kα radiation.

Furthermore, the present invention is directed to a method for preparing a D-form crystal of a fumarate salt of the compound represented by formula (I):

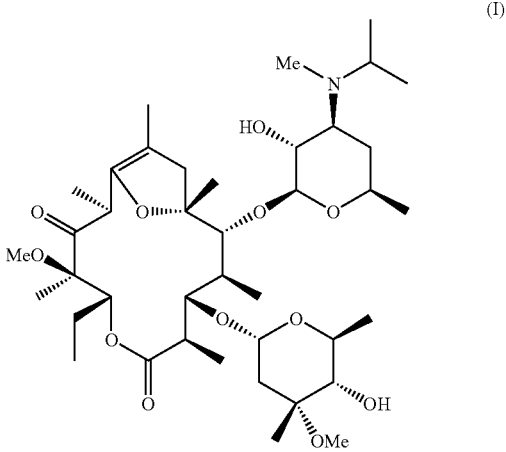

(I)

which comprises obtaining the D-type crystal via an E-type crystal of a fumarate salt of compound (I) having strong X-ray diffraction peaks at diffraction angles (2θ) of 5.6° and 10.4° as measured by X-ray diffractometry with Cu—Kα radiation.

BEST MODE FOR CARRYING OUT THE INVENTION

Figure 1:
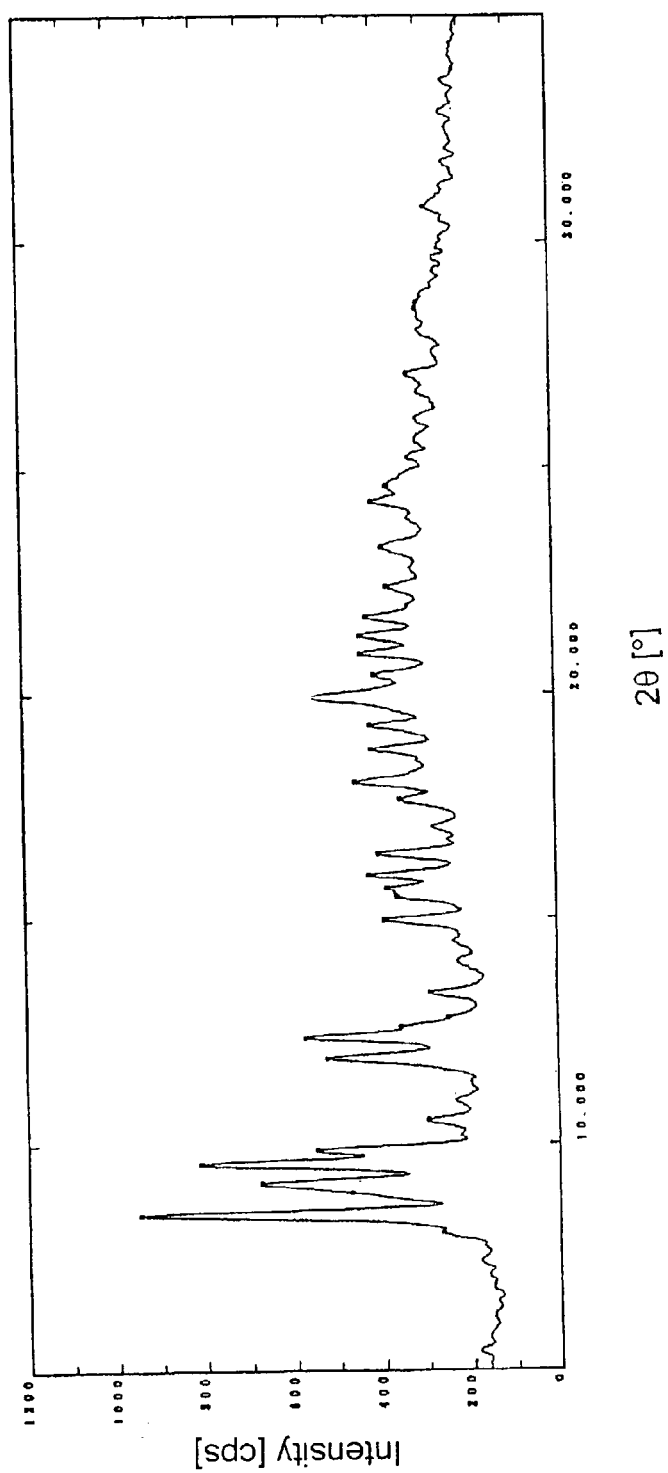
FIG. 1 shows a powder X-ray diffraction pattern of the A-form crystal.
Figure 2:
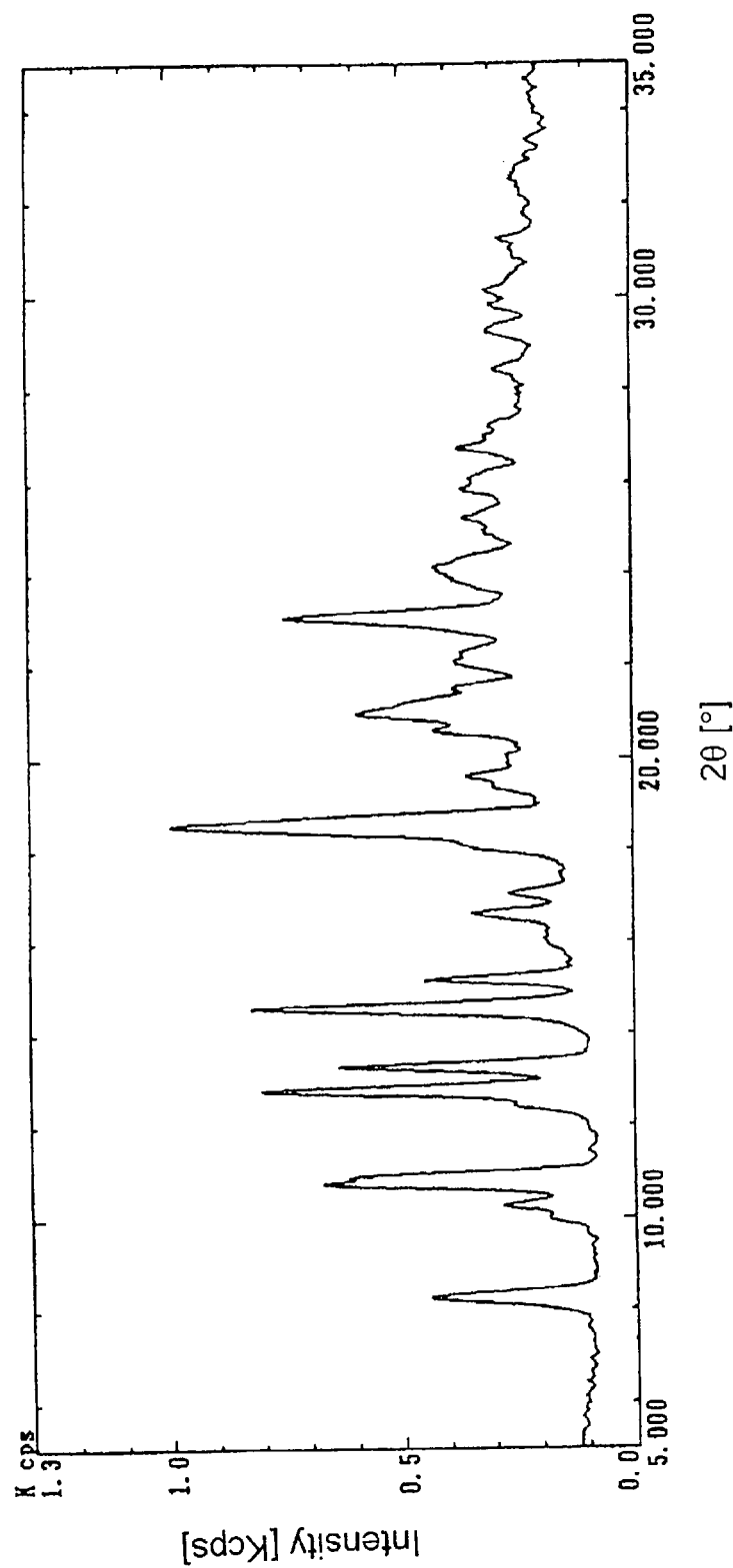
FIG. 2 shows a powder X-ray diffraction pattern of the C-form crystal.
Figure 3:
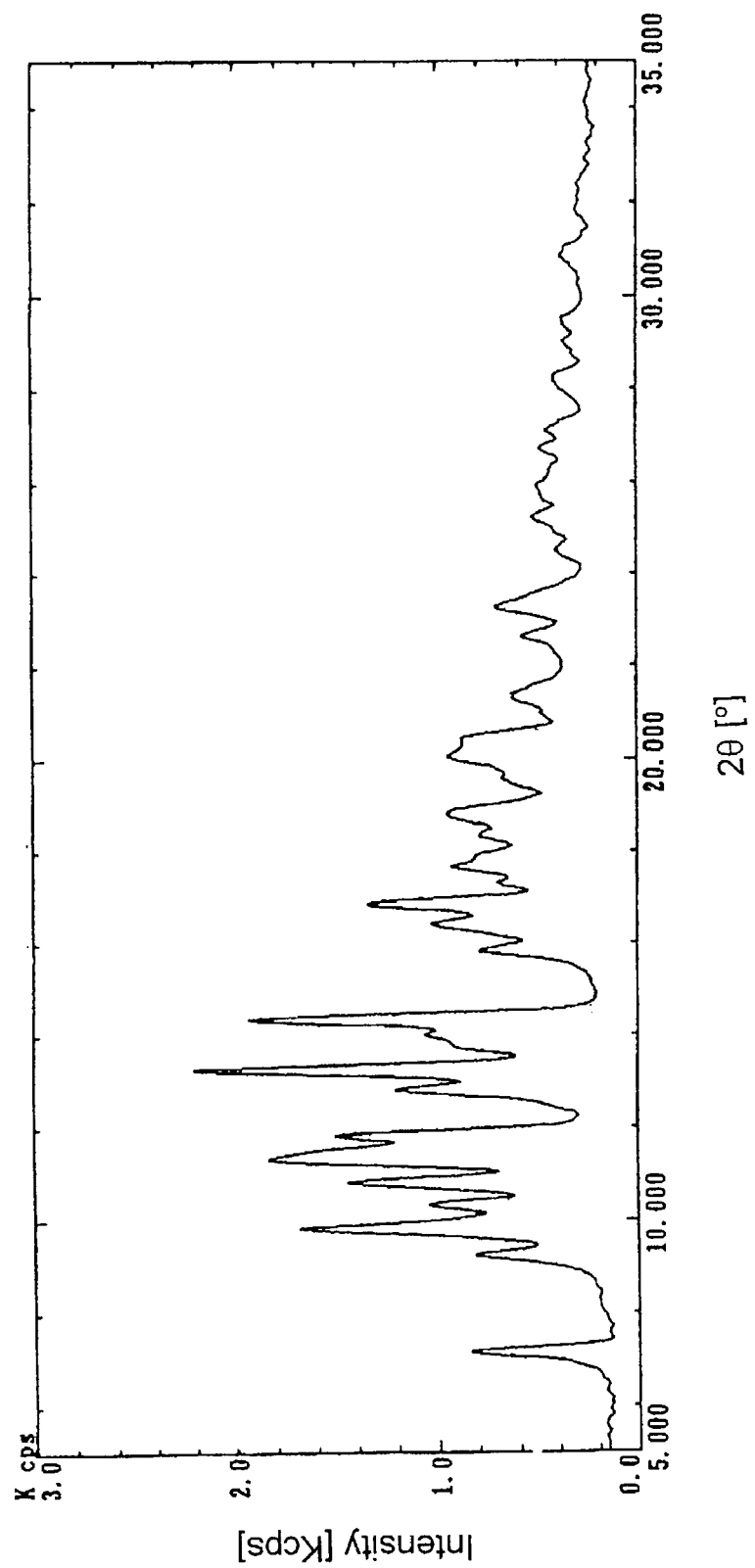
FIG. 3 shows a powder X-ray diffraction pattern of the D-form crystal.
Figure 4:
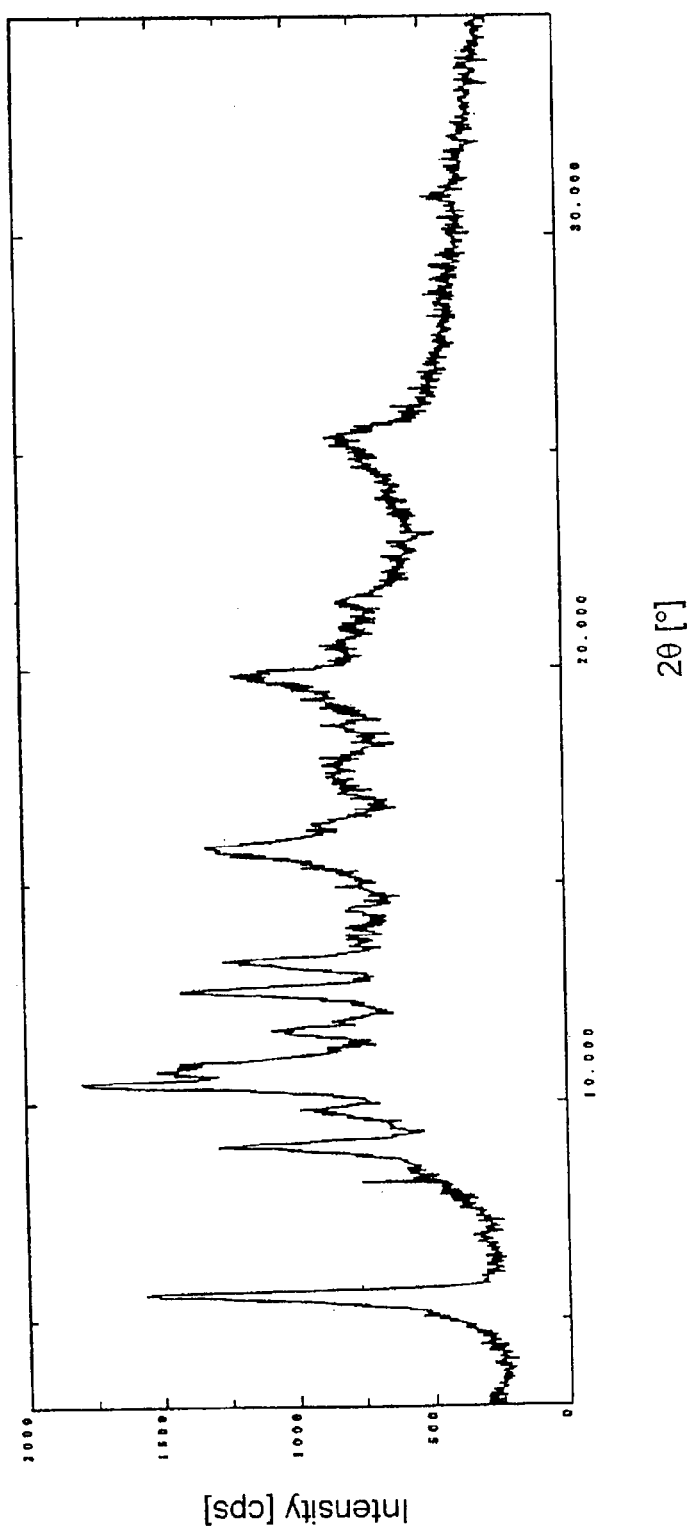
FIG. 4 shows a powder X-ray diffraction pattern of the E-form crystal.

The structurally novel crystal of a fumarate salt of the erythromycin derivative represented by formula (I) according to the present invention (hereinafter simply referred to as "E-type crystal") provides the diffraction pattern as shown in FIG. 4 when measured by X-ray diffractometry with Cu—Kα radiation. FIG. 4 shows strong peaks at diffraction angles (2θ) of 5.6° and 10.4°.

These X-ray diffraction angles can be measured using various devices that are commercially available, such as a powder X-ray diffractometer. The details on the measurement principle of powder X-ray diffractometry can be found in the Japanese Pharmacopoeia, 13th Edition, published by Hirokawa Publishing Co. (1996) pp. B471-B475, the Japanese Pharmacopoeia, 14th Edition, published by Hirokawa Publishing Co. (2001) pp. B614-B619 and elsewhere. In general, the diffraction angle has an acceptable error of around ±0.2°.

As used herein, the term "dryness" refers to the content of residual solvent which reaches an almost unchanged level during drying procedure, more specifically refers to the content at a point where the drying procedure produces a less than 100 ppm/hr decrease in the content of residual solvent.

The present invention will be described below in more detail.

The method for preparing the E-type crystal according to the present invention can start with the C-type crystal.

The C-type crystal may be prepared by treating the A-type crystal with ethyl acetate, as described in JP 9-100241 A.

Further, the A-type crystal may be prepared by treating a fumarate salt of compound (I) with a mixed solvent of methanol and isopropanol, as described in JP 6-56873 A and JP 9-100241 A.

The E-type crystal of the present invention can be prepared by suspending the C-type crystal in a mixed solvent of ethyl acetate and water. The C-type crystal may be used either in isolated crystal or as a suspension in the solvent, but preferably used as a suspension in the solvent. In a preferred embodiment, the A-type crystal is treated with ethyl acetate to yield the C-type crystal as a suspension in ethyl acetate, which is further suspended by addition of water.

In the mixed solvent used in this suspension procedure, the mixing ratio between ethyl acetate and water is usually set to 99:1 to 95:5, preferably 97:3 to 95:5. The suspension procedure is usually performed at a temperature of 20° C. to 40° C., preferably 20° C. to 30° C. A temperature below 20° C. tends to stimulate the conversion into the D-type crystal. The suspension procedure is usually continued for 30 minutes to 300 minutes, preferably 60 minutes to 240 minutes.

The resulting E-type crystal may be separated from the solvent by filtration, centrifugation or the like. The separated E-type crystal may be dried under reduced pressure or other conditions, but preferably dried under reduced pressure. The drying temperature is usually 20° C. to 60° C., preferably 30° C. to 50° C.

The E-type crystal may be suspended in a mixed solvent of ethyl acetate and water at a temperature below 20° C. to yield the D-type crystal. In the mixed solvent used here, the mixing ratio between ethyl acetate and water is preferably set to 99:1 to 97:3. The suspension procedure is preferably performed at a temperature of –20° C. to 20° C. and usually continued for 1 hour to 12 hours, preferably 3 hours to 11 hours, more preferably 5 hours to 10 hours.

In order to prepare the D-form crystal with an average particle size sufficient to avoid tabletting troubles (preferably 90 μm or more, more preferably 100 μm or more) from the E-form crystal, the mixing ratio between ethyl acetate and water is preferably set to 98.1:1.9 to 97:3 in the mixed solvent used for crystallization. The suspension procedure is performed at a temperature of 10° C. to 20° C., preferably 11° C. to 19° C., more preferably 13° C. to 18° C. In order to stimulate the conversion into the D-form crystal or to improve the yield of the D-type crystal, the suspension may further be cooled to –20° C. to 10° C., preferably –15° C. to 10° C. The suspension procedure is usually continued for several minutes to 20 hours, preferably 5 minutes to 4 hours, more preferably 10 minutes to 2 hours. In a case where the suspension is further cooled, the suspension procedure is usually continued for additional several minutes to 20 hours, preferably around 1 hour.

It should be understood that the period of time required for the individual suspension procedures mentioned above refers to the minimum period of time required to prepare the E-form crystal, required to prepare the D-form crystal from the E-form crystal and required to prepare the D-form crystal with a large average particle size from the E-form crystal. The individual suspension procedures may be continued beyond the minimum period of time, depending on the degree of crystal growth or the convenience of preparation steps.

In preparing the D-form crystal via the E-type crystal, the D-form crystal can also be prepared continuously from the C-type crystal via the E-form crystal by merely controlling the temperature, without isolating the E-form crystal during preparation.

The resulting D-form crystal may be separated from the solvent by filtration, centrifugation or the like, and then dried under reduced pressure. The drying temperature is preferably 20° C. to 70° C. The D-form crystal of the present invention may completely (100%) or partially be composed of compound molecules prepared via the E-form crystal. In the latter case, the D-form crystal prepared via the E-form crystal may be contained at any percentage as long as the content of residual solvent does not exceed 1500 ppm, preferably not exceed 1000 ppm, and/or tabletting troubles do not occur.

The D-form crystal prepared via the E-form crystal in this way ensures a residual solvent content of 1500 ppm or below, which could not be achieved by the prior art D-form crystal. In addition, the D-form crystal thus prepared further ensures a residual solvent content of 1000 ppm or below and is also easier to dry than the prior art D-form crystal; it is therefore more preferable as an active pharmaceutical ingredient. The D-form crystal partially prepared via E-form crystal also ensures a residual solvent content of 1500 ppm or below, which could not be achieved by the prior art D-form crystal. This D-form crystal further ensures a residual solvent content of 1000 ppm or below and is also easier to dry than the prior art D-form crystal; it is also therefore more preferable as an active pharmaceutical ingredient.

Further, the D-form crystal with a large average particle size prepared under the conditions mentioned above cannot be obtained by the prior art techniques and allows avoidance of tabletting troubles; it is therefore particularly advantageous in preparing pharmaceuticals.

The content of residual solvent may be determined in a known manner, for example, by gas chromatography. The details on gas chromatography can be found in the Japanese Pharmacopoeia, 13th Edition, published by Hirokawa Publishing Co. (1996) pp. B83-B94, the Japanese Pharmacopoeia, 14th Edition, published by Hirokawa Publishing Co. (2001) pp. B98-B114 and elsewhere. In general, gas chromatography will cause a measurement error falling within around ±1%. The compound of the present invention can also be determined for its average particle size in a known manner or using various devices that are commercially available, such as a dry particle size distribution analyzer. In general, such a particle size distribution analyzer will cause a measurement error falling within around ±5%.

EXAMPLES

The present invention will be further described in the following examples, which are provided for illustrative purposes only and are not intended to limit the scope of the invention.

In these examples and comparison examples, X-ray diffractometry was performed using a powder X-ray diffractometer RINT-1100 (Rigaku), the content of residual solvent was determined using a gas chromatograph GC-17A (Shimadzu Corp.), and the average particle size was determined using a particle size distribution analyzer RPS-95 (Seishin Enterprise Co., Ltd.). The content of residual solvent had a measurement error of around ±1%, while the average particle size had a measurement error of around ±4%.

Example 1

Figure 5:
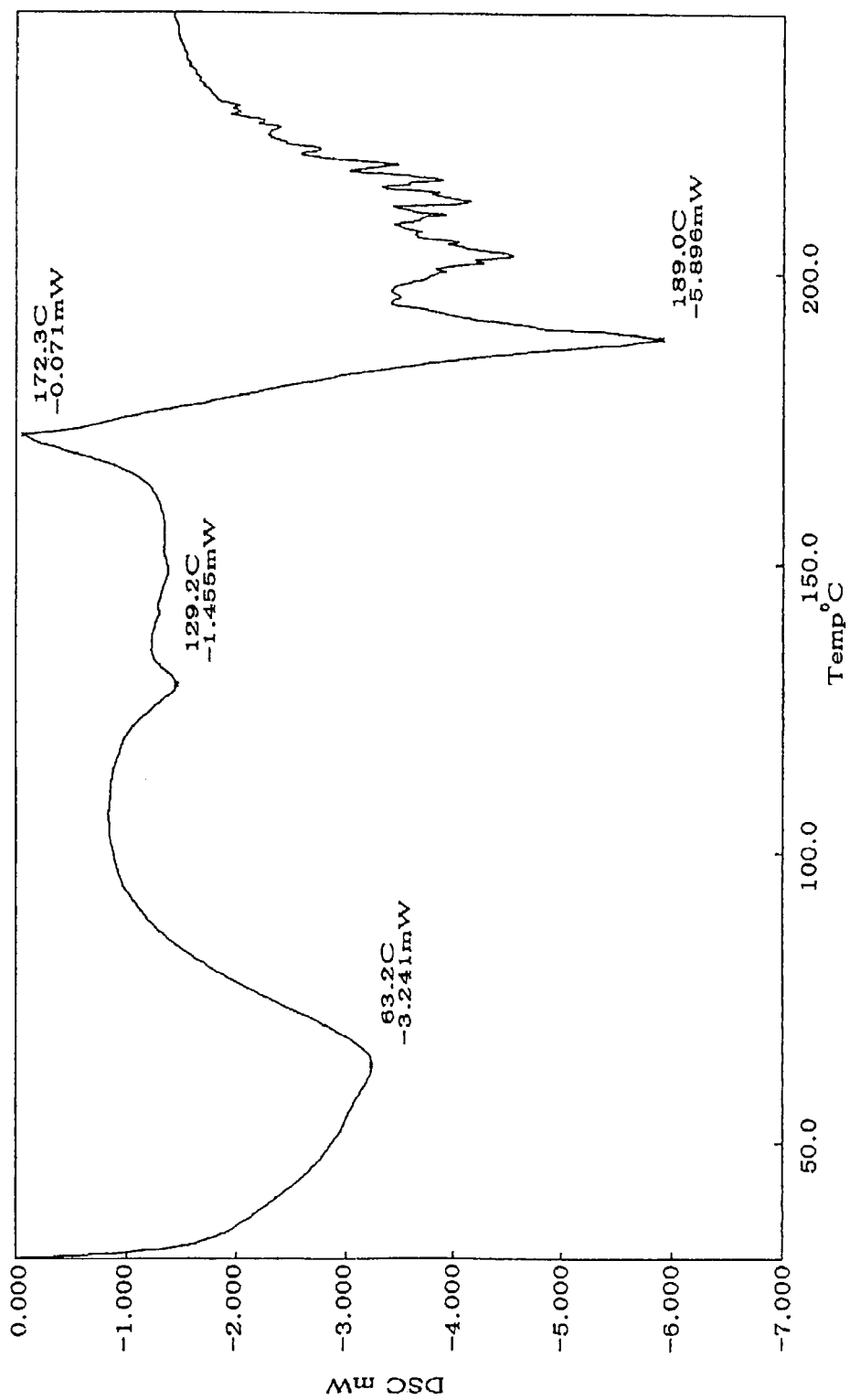
FIG. 5 shows a DSC spectrum of the E-form crystal.

A fumarate salt of compound (I) (50.0 g) was dissolved in ethyl acetate (400 mL) and methanol (40 mL) at room temperature. The solution was then concentrated to dryness under reduced pressure at room temperature. The resulting dried product was stirred in ethyl acetate (415 mL) at 25° C. for 1 hour to give a suspension of a C-form crystal. Water (4.15 mL) was added to this suspension, followed by stirring at 25° C. for 0.5 hours. Water (4.15 mL) was further added and stirred at 25° C. for 0.5 hours. Water (4.15 mL) was further added and stirred at 25° C. for 0.5 hours. Water (4.15 mL) was further added and stirred at 25° C. for 0.5 hours. The suspension was then cooled to 20° C., stirred for 1 hour, and filtered to give a wet crystal (43.7 g). This wet crystal was dried under reduced pressure at 40° C. for 3 hours to give a crystal of the fumarate salt of compound (I) (34.1 g). This crystal was confirmed to be an E-form crystal having strong peaks at diffraction angles (2θ) of 5.6° and 10.4° as measured by X-ray diffractometry. FIG. 5 shows a DSC spectrum of the resulting E-form crystal.

Example 2

A fumarate salt of compound (I) (20 g) was stirred in ethyl acetate (166 mL) at 25° C. for 2 hours to give a C-form crystal. After addition of water (2.4%, 4.0 mL), this C-form crystal was gradually cooled to ensure its complete conversion into E-form. The suspension was further cooled to 15° C. and stirred for 3 hours, followed by cooling to −10° C. The resulting crystal was then isolated to give a wet D-form crystal (20.4 g, average particle size: 302 μm). This wet D-form crystal was dried under reduced pressure at 25° C. for 1 hour and further dried at 60° C. to give the D-form crystal of the fumarate salt of compound (I). The resulting D-form crystal was found to have a residual solvent content of 78 ppm.

Example 3

Starting with a C-form crystal of a fumarate salt of compound (I), the same procedures as shown in Example 2 were repeated, except for adding 2.6% water, to give a D-form crystal with a particle size of 197 μm via an E-form crystal.

Example 4

A fumarate salt of compound (I) (11.6 kg) was dissolved at 25° C. in a mixed solvent of ethyl acetate (104.6 kg) and methanol (9.2 kg). After the solution was concentrated, ethyl acetate (86.8 kg) was added at 25° C. to the concentrated residue, followed by stirring at 24° C. for 1 hour to give a C-form crystal. After addition of water (2.0%, 1.9 kg), this C-form crystal was gradually cooled to ensure its conversion into E-form crystal. The suspension was further cooled to 15° C. and stirred for 1 hour, followed by cooling to −10° C. The resulting crystal was then centrifuged to give a wet D-form crystal (13.4 kg). This wet D-form crystal was dried under reduced pressure at 60° C. for 28 hours to give the D-form crystal of the fumarate salt of compound (I) (10.5 kg, yield 90.5%, average particle size: 141 μm). The resulting D-form crystal was found to have a residual solvent content of 988 ppm. In addition, no tabletting trouble was observed in this D-form crystal when used as a main component to prepare tablets.

Example 5

A fumarate salt of compound (I) (11.6 kg) was dissolved at 30° C. in a mixed solvent of ethyl acetate (94.2 kg) and methanol (9.1 kg). After the solution was concentrated, ethyl acetate (86.8 kg) was added at 22° C. to the concentrated residue, followed by stirring at 24° C. for 1 hour to give a C-form crystal. After addition of water (2.0%, 1.9 kg), this C-form crystal was gradually cooled to ensure its conversion into E-form crystal. The suspension was further cooled to 15° C. and stirred for 1 hour, followed by cooling to −10° C. The resulting crystal was then centrifuged to give a wet D-form crystal (13.2 kg). This wet D-form crystal was dried under reduced pressure at 60° C. for 10 hours to give the D-form crystal of the fumarate salt of compound (I) (10.5 kg, yield 90.5%, average particle size: 197 μm). The resulting D-form crystal was found to have a residual solvent content of 845 ppm. In addition, no tabletting trouble was observed in this D-form crystal when used as a main component to prepare tablets.

C-form crystals of a fumarate salt of compound (I) were similarly treated in accordance with Example 4 or 5 to give D-form crystals via E-form crystals (Examples 6 to 8).

Comparison Example 1

A fumarate salt of compound (I) (10.8 kg) was dissolved at 25° C. in a mixed solvent of ethyl acetate (87.6 kg) and methanol (8.5 kg). After the solution was concentrated, ethyl acetate (80.8 kg) was added at 25° C. to the concentrated residue, followed by stirring at 25° C. for 1 hour to give a C-form crystal. After addition of water (1.5%, 1.3 kg), this C-form crystal was cooled to 15° C. and stirred for 1 hour to ensure its conversion into D-form crystal. The suspension was further cooled to −10° C. and stirred for 1 hour. The resulting crystal was then centrifuged to give a wet D-form crystal (12.7 kg). This wet D-form crystal was dried under reduced pressure at 60° C. for 16 hours to give the D-form crystal of the fumarate salt of compound (I) (10.8 kg, yield 87.4%, average particle size: 82 μm). Tabletting troubles were observed in this D-form crystal when used as a main component to prepare tablets.

A C-form crystal of a fumarate salt of compound (I) was similarly treated in accordance with Comparison Example 1 to give a D-form crystal without going via an E-form crystal (Comparison Example 2).

Table 1 summarizes the properties of the D-form crystals prepared via E-form crystals (Examples 2 to 8) and the prior art D-type crystals (Comparison Examples 1 and 2).

TABLE 1

| | Percentage of water (%) | Prepared via E-form crystal | Conditions for conversion of E-form crystal into D-form crystal | Drying conditions | Content of residual solvent (ppm) | Particle size (μm) | Tabletting trouble |
|---|---|---|---|---|---|---|---|
| Example 2 | 2.4 | Completely | 15° C., 3 hr → −10° C. | Reduced pressure 60° C., 8 hr | 78 | 302 | — |
| Example 3 | 2.6 | Completely | 15° C., 6 hr → −10° C. | Reduced pressure 60° C., 8 hr | — | 197 | — |
| Example 4 | 2.0 | Partially | 15° C., 1 hr → −10° C. | Reduced pressure 60° C., 28 hr | 988 | 141 | No |
| Example 5 | 2.0 | Partially | 15° C., 1 hr → −10° C. | Reduced pressure 60° C., 10 hr | 845 | 197 | No |

TABLE 1-continued

| | Percentage of water (%) | Prepared via E-form crystal | Conditions for conversion of E-form crystal into D-form crystal | Drying conditions | Content of residual solvent (ppm) | Particle size (μm) | Tabletting trouble |
|---|---|---|---|---|---|---|---|
| Example 6 | 2.0 | Partially | 13° C., 0.5 hr → −10° C. | Reduced pressure 60° C., 9 hr | 1049 | — | — |
| Example 7 | 2.0 | Partially | 15° C., 1 hr → −10° C. | Reduced pressure 60° C., 6 hr | 647 | 163 | No |
| Example 8 | 2.0 | Partially | 15° C., 1 hr → −10° C. | Reduced pressure 60° C., 10 hr | 893 | 185 | No |
| Comparison Example 1 | 1.5 | Not | — | Reduced pressure 60° C., 16 hr | 2228 | 82 | Yes |
| Comparison Example 2 | 1.5 | Not | — | Aeration 45° C., 20 hr | 1610 | 61 | Yes |

INDUSTRIAL APPLICABILITY

The E-form crystal of a fumarate salt of compound (I) according to the present invention enables the preparation of the D-form crystal with superior properties including a reduced content of residual solvent and high suitability for formulation. More specifically, the E-form crystal is characterized by (1) providing pharmaceuticals with superior quality and (2) allowing the efficient preparation of pharmaceuticals; it is therefore extremely useful in pharmaceutical preparation.

The invention claimed is:

1. An isolated E-form crystal which is obtained by treating a C-form crystal of a fumarate salt of the compound represented by formula(I):

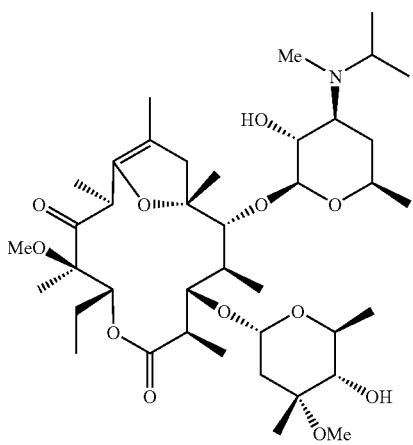

(I)

in a mixed solvent of ethyl acetate and water, wherein said E-form crystal has strong X-ray diffraction peaks at diffraction angles (2θ) of 5.6°, 10.4°, 12.5°, 15.8° and 19.9° as measured by X-ray difractometry with Cu—Kα radiation, and wherein the content of water is 2.4% to 5% in the mixed solvent of ethyl acetate and water.

2. The isolated E-form crystal according to claim 1 wherein said treating is performed at 20° to 40° C.

3. The isolated E-form crystal according to claim 2 wherein the content of water in the mixed solvent is 2.4 to 2.6%.

4. An isolated E-form crystal of a fumarate salt of the compound represented by formula I

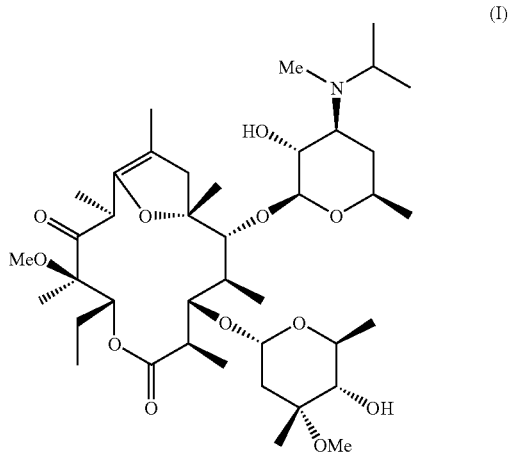

(I)

wherein the E-form crystal has strong X-ray diffraction peaks at diffraction angles (2θ) of 5.6°, 10.4°, 12.5°, 15.8° and 19.9° as measured by X-ray diffractometry with Cu—Kα radiation.

5. The isolated E-form crystal according to claim 1 or 4 wherein said E-form crystal has strong X-ray diffraction peaks at diffraction angles (2θ) of 5.6°, 9.0°, 10.4°, 12.5°, 13.2°, 15.8° and 19.9° as measured by X-ray diffractometry with Cu—Kα radiation.

* * * * *